United States Patent
Youssefi et al.

(10) Patent No.: US 9,186,059 B2
(45) Date of Patent: Nov. 17, 2015

(54) OPHTHALMIC INSTRUMENT ALIGNMENT APPARATUS AND METHOD OF USING SAME

(75) Inventors: Gerhard Youssefi, Landshut (DE); Rupert Veith, Pfarrkirchen (DE)

(73) Assignee: Bausch & Lomb Incorporated, Rochester, NY (US)

( * ) Notice: Subject to any disclaimer, the term of this patent is extended or adjusted under 35 U.S.C. 154(b) by 1226 days.

(21) Appl. No.: 12/334,896

(22) Filed: Dec. 15, 2008

(65) Prior Publication Data
US 2009/0161067 A1 Jun. 25, 2009

Related U.S. Application Data

(60) Provisional application No. 61/015,781, filed on Dec. 21, 2007.

(51) Int. Cl.
*A61B 3/15* (2006.01)
*A61F 9/008* (2006.01)

(52) U.S. Cl.
CPC .................. *A61B 3/152* (2013.01); *A61F 9/008* (2013.01); *A61F 2009/00872* (2013.01)

(58) Field of Classification Search
USPC .......... 351/200, 205, 206, 208, 211–212, 246
See application file for complete search history.

(56) References Cited

U.S. PATENT DOCUMENTS

| | | |
|---|---|---|
| 4,869,593 A | 9/1989 | Biegen |
| 4,938,584 A | 7/1990 | Suematsu et al. |
| 5,042,938 A | 8/1991 | Shimozono |
| 5,098,426 A * | 3/1992 | Sklar et al. ............... 351/209 |
| 5,141,302 A | 8/1992 | Arai et al. |
| 5,280,313 A | 1/1994 | Kohayakawa |
| 5,282,852 A | 2/1994 | Capetan et al. |
| 5,301,010 A | 4/1994 | Jones et al. |
| 5,347,327 A * | 9/1994 | Sekine et al. ............. 351/211 |
| 5,387,951 A | 2/1995 | Hatanaka |

(Continued)

FOREIGN PATENT DOCUMENTS

| | | |
|---|---|---|
| DE | 102005006897 A1 | 8/2006 |
| EP | 0956809 A1 | 11/1999 |

(Continued)

OTHER PUBLICATIONS

Michelson, Albert A., and Edward W. Morley. "On the Relative Motion of the Earth and the Luminiferous Ether." American Journal of Science XXXIV.203 (Nov. 1887): 333-345.*

(Continued)

*Primary Examiner* — Zachary Wilkes
(74) *Attorney, Agent, or Firm* — Toan P. Vo

(57) ABSTRACT

An ophthalmic instrument for use with a subject's eye, comprising an interferometer having a test arm in which the subject's eye is to be positioned and a reference arm, the reference arm including a mirror adapted to be positioned such that the reference arm has a predetermined length, and an ophthalmic apparatus coupled to the interferometer such that, by altering a test arm length, a length between the ophthalmic apparatus and the eye is also altered. The mirror is positioned to achieve the predetermined length and a length of the test arm is adjusted such that interference between the light reflected from the eye and the light reflected from the mirror is achieved, the ophthalmic apparatus is optically aligned with the eye.

21 Claims, 3 Drawing Sheets

(56) References Cited

U.S. PATENT DOCUMENTS

| | | | |
|---|---|---|---|
| 5,481,359 A * | 1/1996 | Barker | 356/519 |
| 5,633,694 A * | 5/1997 | Mihashi et al. | 351/211 |
| 5,673,096 A | 9/1997 | Dorsel et al. | |
| 5,719,673 A | 2/1998 | Dorsel et al. | |
| 5,847,827 A | 12/1998 | Fercher | |
| 5,870,191 A | 2/1999 | Shirley et al. | |
| 5,973,781 A | 10/1999 | Moeller et al. | |
| 5,975,699 A | 11/1999 | Hellmuth | |
| 6,050,687 A * | 4/2000 | Bille et al. | 351/212 |
| 6,053,613 A | 4/2000 | Wei et al. | |
| 6,057,920 A | 5/2000 | Fercher et al. | |
| 6,144,456 A | 11/2000 | Chavanne et al. | |
| 6,243,191 B1 | 6/2001 | Fercher | |
| 6,384,945 B1 | 5/2002 | Hakimi et al. | |
| 6,407,872 B1 | 6/2002 | Lai et al. | |
| 6,454,761 B1 | 9/2002 | Freedman | |
| 6,601,956 B1 | 8/2003 | Jean et al. | |
| 6,724,487 B2 | 4/2004 | Marcus et al. | |
| 6,779,891 B1 | 8/2004 | Barth et al. | |
| 7,016,046 B2 | 3/2006 | Hauger | |
| 7,079,255 B2 | 7/2006 | Fercher | |
| 7,084,986 B2 | 8/2006 | Hellmuth et al. | |
| 7,246,905 B2 | 7/2007 | Benedikt et al. | |
| 2002/0163623 A1 | 11/2002 | Hirohara et al. | |
| 2004/0021874 A1 | 2/2004 | Shimmick | |
| 2004/0061830 A1 | 4/2004 | Hellmuth et al. | |
| 2004/0070730 A1 | 4/2004 | Mihashi et al. | |
| 2005/0140981 A1 | 6/2005 | Waelti | |
| 2005/0203422 A1 | 9/2005 | Wei | |
| 2006/0146334 A1 | 7/2006 | Cluff et al. | |
| 2006/0279698 A1 * | 12/2006 | Muhlhoff et al. | 351/208 |
| 2007/0291276 A1 | 12/2007 | Fercher | |

FOREIGN PATENT DOCUMENTS

| | | |
|---|---|---|
| EP | 1702595 A1 | 9/2006 |
| EP | 1842482 A2 | 10/2007 |
| GB | 2370877 A | 7/2002 |
| JP | 2297332 A | 12/1990 |
| WO | WO 83/03684 A1 | 10/1983 |
| WO | WO 93/20743 A1 | 10/1993 |
| WO | WO 02/064031 A2 | 8/2002 |
| WO | WO 03/002936 A1 | 1/2003 |
| WO | WO 03/052345 A1 | 6/2003 |
| WO | WO 03/077739 A2 | 9/2003 |
| WO | 2004/057266 A2 | 7/2004 |
| WO | 2004/084719 A1 | 10/2004 |
| WO | 2005/045362 A1 | 5/2005 |
| WO | 2005/060823 A1 | 7/2005 |
| WO | 2005/074789 A1 | 8/2005 |
| WO | 2005/114094 A1 | 12/2005 |
| WO | 2006/081988 A1 | 8/2006 |
| WO | 2006/081998 A1 | 8/2006 |

OTHER PUBLICATIONS

Ohmi et al., "In-situ observation of tissue laser ablation using optical coherence tomography," Opt and Quntum Elec, 2005, (vol. 37), (p. 1175-1183).

* cited by examiner

OPHTHALMIC INSTRUMENT ALIGNMENT APPARATUS AND METHOD OF USING SAME

CROSS-REFERENCE

This application claims the benefit of Provisional Patent Application No. 61/015,781 filed Dec. 21, 2007 which is incorporated by reference herein.

FIELD OF INVENTION

The present invention relates to ophthalmic instrument alignment apparatus and methods of use.

BACKGROUND OF THE INVENTION

Some ophthalmic procedures use highly precise diagnostic apparatus and/or surgical apparatus. To take advantage of the precision, it is important that the apparatus be accurately aligned with a subject's eye.

Various alignment apparatus are known. FIG. 1 is a schematic illustration of one conventional apparatus for axial alignment with a subject's eye. A first laser 10 and a second laser 20 are aligned so that the beams from the lasers intersect at a location L. The eye is brought to a longitudinal location L (in the z-direction) by observing an image of the light in the beams that is scattered by the subject's cornea C. The image is formed using a camera 50. When two spots $R_1$ and $R_2$ are observed by the camera, the subject's eye is either in front of or behind location L; and when a single spot is observed the subject's eye is proximate location L and assumed to be axially aligned. Such alignment apparatus have limitation on the degree of accuracy with which an instrument can be consistently aligned.

SUMMARY

Aspects of the present invention are directed to an ophthalmic instrument that is precisely axially positionable relative to a subject's eye. The instrument typically includes an interferometer to facilitate axial alignment and another ophthalmic apparatus (e.g., an ablation laser or a diagnostic apparatus) which is axially aligned when the instrument is precisely positioned.

Embodiments of instruments according to such aspects comprise an interferometer having a test arm configured to project light onto an eye, and a reference arm including a mirror positioned such that the reference arm has a predetermined length. The mirror may be movable to achieve the predetermined length or may be fixed in an appropriate location to provide the predetermined length.

At least a portion of the instrument is movable relative to the eye such that a length of the test arm can be adjusted and such that a distance between the apparatus and the eye is also altered. Accordingly, the at least portion of the instrument is moved such that interference between the light reflected from the surfaces of the eye and the light reflected from the mirror is achieved, thereby aligning the ophthalmic apparatus with the eye.

According to aspects of the present invention, in an ophthalmic instrument comprising 1) an interferometer with a reference arm and a test arm, and 2) an ophthalmic apparatus (e.g., an ablation laser or a diagnostic apparatus), the interferometer is used to generate interference between light reflected from a surface of an eye in the test arm and light reflected from a mirror in the reference arm thereby aligning the ophthalmic apparatus relative to the eye.

An aspect of the invention is directed to an ophthalmic instrument for use with a subject's eye comprising an interferometer having a test arm in which the subject's eye is to be positioned and a reference arm, the reference arm including a mirror adapted to be positioned such that the reference arm has a predetermined length, and an ophthalmic apparatus coupled to the interferometer such that, by altering a test arm length, a length between the ophthalmic apparatus and the eye is also altered. In embodiments according to such aspects, when the mirror is positioned to achieve the predetermined length and a length of the test arm is adjusted such that interference between the light reflected from the eye and the light reflected from the mirror is achieved, the ophthalmic apparatus is optically aligned with the eye.

In some embodiments, the apparatus comprises at least one of: a portion of an ablation laser apparatus, a portion of an aberrometer, a portion of a topographer, and a portion of a pachymeter. In some embodiments, the interferometer constitutes a portion of a device used to measure an axial eye length.

The instrument may further comprise a processor coupled to the mirror and configured to position the mirror. The mirror may be adapted to be manually positioned.

In some embodiments, the optical components of the interferometer and optical components of the apparatus are connected to a common platform. In some embodiments, the optical components of the interferometer and optical components of the apparatus are disposed in and connected to a housing.

In some embodiments, a portion of the instrument is adapted to be moved to achieve alignment with the eye. In some embodiments, the instrument is adapted to move the eye to achieve alignment with the eye.

In some embodiments, the instrument is adapted to move the mirror in an oscillatory manner, such that the predetermined length is achieved at a particular time, and optical alignment of the ophthalmic apparatus with the eye is achieved when the test arm length is adjusted such that the interference occurs at the particular time.

Another aspect of the invention is directed to a method of alignment, comprising (A) providing an ophthalmic instrument comprising an ophthalmic apparatus and an interferometer having a test arm and a reference arm, the reference arm including a mirror, the ophthalmic apparatus coupled to the interferometer such that, when a test arm length is altered, a length between the ophthalmic apparatus and the eye is also altered, (B) positioning the mirror such that the reference arm has a predetermined length, (C) projecting partially coherent light, a first portion of the light directed onto an eye in the test arm, and a second portion of the light directed onto the mirror in the reference arm, (D) combining a portion of the light reflected from the eye and a portion of the light reflected from the mirror, and (E) adjusting a length of the test arm such that interference between the light reflected from the eye and the light reflected from the mirror is achieved and optical alignment of the ophthalmic apparatus with the eye is achieved.

In some embodiments, in the step of providing, the ophthalmic apparatus comprises at least one of: a portion of an ablation laser apparatus, a portion of an aberrometer, a portion of a topographer, and a portion of a pachymeter. In some embodiments, in the step of providing, the interferometer constitutes a portion of a device used to measure an axial eye length.

In some embodiments, the method further comprises a step of using a processor to position the mirror to achieve the predetermined length. In some embodiments, the method further comprises a step of manually positioning the mirror to achieve the predetermined length.

In some embodiments, the method further comprises moving the mirror in an oscillatory manner, such that the predetermined length is achieved at a particular time, and wherein the step of adjusting comprises adjusting the test arm length until the interference occurs at the particular time.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
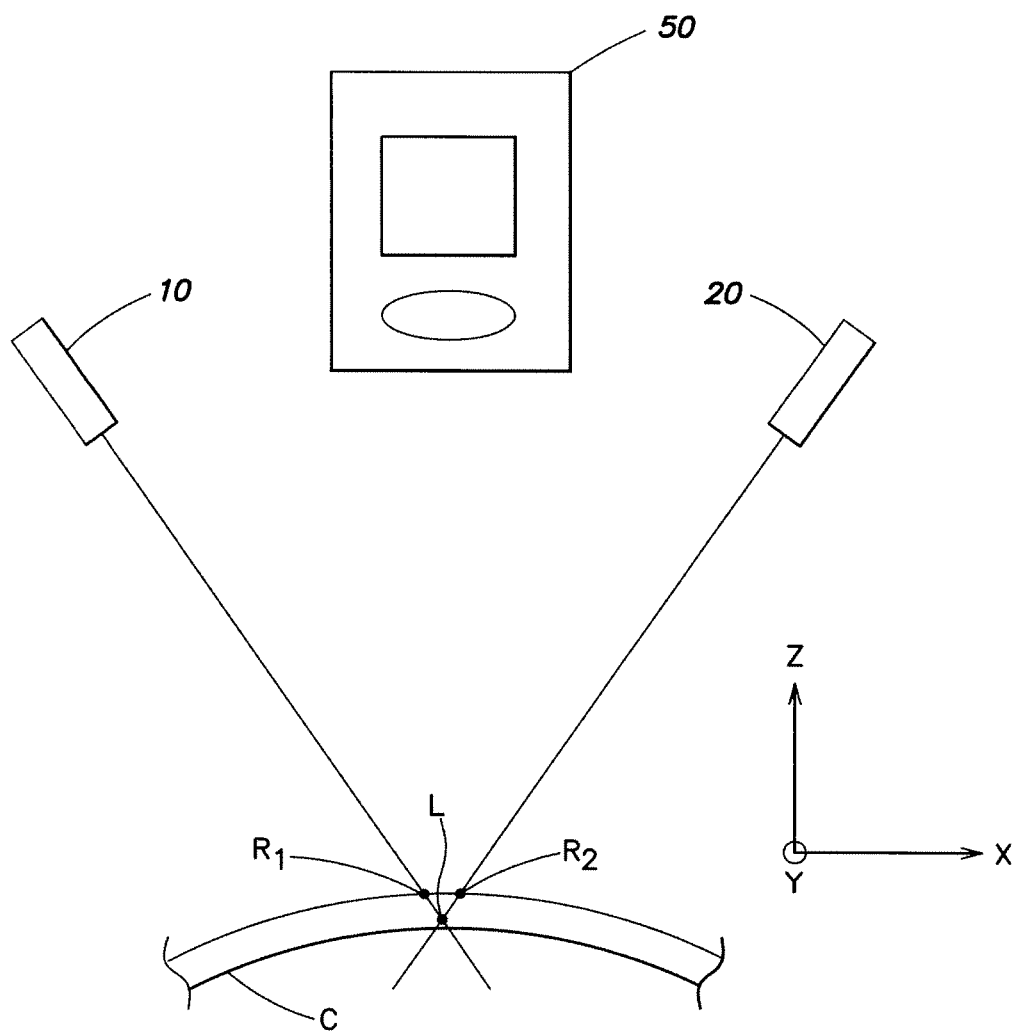
FIG. 1 is a schematic illustration of a conventional apparatus for axial alignment with a subject's eye.
Figure 2A:
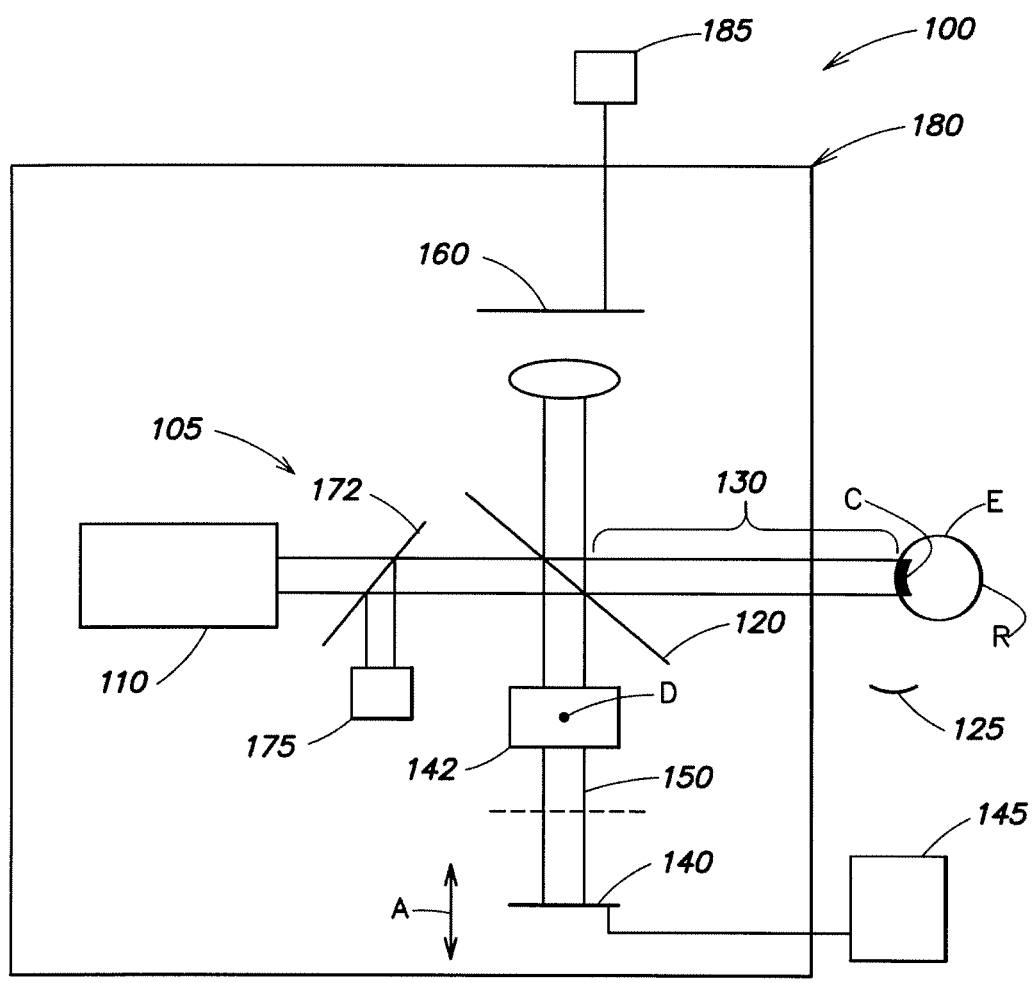
FIG. 2A is a schematic illustration of an example of an ophthalmic instrument according to aspects of the present invention.

FIG. 2A is a schematic illustration of an ophthalmic instrument 100 according to aspects of the present invention for use with a subject's eye E. The instrument comprises an interferometer 105 and an ophthalmic apparatus 175. The interferometer and the device are configured and arranged such that an adjustment of a length of a test arm 130 of the interferometer relative to eye E results in a corresponding adjustment of an optical distance from ophthalmic apparatus 175 to eye E. For example, instrument 175 can comprise an ablation laser for performing refractive surgery, at least a portion of an ophthalmic aberrometer, a topographer or a pachymeter.

In interferometer 105, light from a source 110 is projected onto a beam splitter 120 which projects light onto an eye E in test arm 130 and onto a mirror 140 in a reference arm 150. Light reflected from the eye and light reflected from the mirror are projected onto a detector 160. The light has a coherence length determined by the source construction.

An output signal from detector 160 is generated by the combined reflections (of light from source 110) by the eye E and mirror 140. The amplitude of the signal will increase and decrease due to interference (i.e., interference spikes will be generated) when the length of the reference arm is within a distance equal to the coherence length of the light of a length of the test arm. A length of the test arm is determined by a reflective surface in the eye (e.g., a surface of the cornea). Typically, source 110 is selected to have a short coherence length, so that interference occurs when the length of the reference arm is very nearly equal to the length of the test arm. For example, the source may be superluminescent diode. In some embodiments, the coherence length of the light source is less than about 10 microns.

In some embodiments, the interferometer constitutes at least a portion of a device used to measure eye dimensions or to perform anther ophthalmic function. In other embodiments, the interferometer is included in instrument 100 exclusively for alignment purposes. In embodiments where the interferometer constitutes a portion of a device used to measure eye dimensions, the interferometer may constitute a portion of an axial eye length measurement device or an optical coherence tomography device. Such device, typically, make eye measurements using a Michelson interferometer arrangement as shown in FIG. 2.

As one of ordinary skill in the art would understand, in device used to measure eye dimensions, the amount which the mirror 140 is moved (e.g., scanned by a motorized device) between a location to achieve an interference output for a first surface (e.g., a surface of the cornea) and a location to achieve an interference output for a second surface (e.g., a surface of the retina) indicates the distance between the first surface and the second surface. For example, an eye's overall axial length can be measured in this manner. It will be appreciated that according to aspects of the present invention, in embodiments where the interferometer constitutes a portion of a device used to measure eye dimensions, the apparatus is put to further use as an alignment apparatus.

According to aspects of the present invention, mirror 140 is positioned such that the reference arm (the span from the beam splitter to the mirror) has a predetermined length. For example, the mirror may be precisely positioned using a servomotor or a fixed mechanical stop. In some embodiments (as illustrated in FIG. 2A), the positioning may be achieved using a suitably programmed processor 145 to position the mirror. In other embodiments, mirror 140 may be moved using a manually operated stage (not shown). In embodiments where the predetermined length is to be achieved manually, a visual indicator indicative of the length may be provided. In yet other embodiments, the mirror may be positioned in a fixed location (e.g., the reference arm has a fixed length set during manufacture of the instrument).

Once the mirror is appropriately positioned such that the predetermined reference arm length is achieved, the test arm is adjusted relative to eye E (which results in a corresponding adjustment of a distance from the ophthalmic apparatus to the eye) to achieve alignment. In particular, the adjustment of the test arm is made to achieve interference between the light reflected from a given surface of the eye and the light reflected from the mirror. Typically, the surface used for alignment is the anterior corneal surface; however, other eye surfaces can be used. In the illustrated embodiment, the positioning is achieved using processor 145; however, in some embodiments, the mirror may be moved using a manually operated stage (not shown).

As stated above, according to aspects of the present invention, ophthalmic apparatus 175 is coupled to interferometer 105 such that, by altering a length of test arm 130, an optical length between the ophthalmic apparatus and the eye is also altered. In the illustrated embodiment, the optical length of the test arm is determined by the length from the given surface of the eye to beam splitter 172, and the optical length between the apparatus 175 and the eye is determined in part the length from the given surface of the eye to beam splitter 172. Accordingly, it will be appreciated that, by altering the test arm length, ophthalmic apparatus 175 can be axially aligned with eye E.

Typically, instrument 100 is configured such that, when the test arm is made to achieve interference between the light reflected from a surface of the eye and the light reflected from mirror 140, ophthalmic apparatus 175 is operatively positioned relative to the eye. For example, in embodiments where the ophthalmic apparatus is an ablation laser, the laser is suitably focused on the cornea of the eye; in embodiments where the apparatus is an aberrometer (comprising a laser beam injection apparatus and a detection camera), the laser beam light injection apparatus is suitably focused on the eye (e.g., a surface of the retina) and/or the detection camera is suitably positioned to receive a focused image of light reflected from the eye; and in embodiments where the ophthalmic apparatus is slit camera pachymeter, slits of light are suitably projected on eye the and/or a camera is suitably positioned to receive focused images of the slits of light after they impinge on the eye.

Alignment of instrument 100 and eye E can be achieved by moving the instrument 100, eye E or both. In some embodiments, particularly where the instrument is to be moved to achieve alignment, optical components of the interferometer 105 are connected to optical components of apparatus 175 such that by altering a length of test arm, a length between the ophthalmic apparatus and the eye is also altered. For example, in some embodiments, suitable optical components of the interferometer and suitable optical components of the ophthalmic apparatus are connected to a common platform 180 such that by altering a length of test arm 130, an optical length between ophthalmic apparatus 175 and the eye is also altered. In the illustrated example, source 110, beam splitter 120, detector 160 and mirror 140 are disposed on a platform 180, and optical components of ophthalmic apparatus 175 are disposed on the platform. It will be appreciated that apparatus according to aspects of the present invention are configured to facilitate optical alignment, and as such electronic components of either the interferometer or the ophthalmic apparatus can be configured to move with the optics or may remain stationary or may be otherwise moved.

Although in the illustrated embodiment, the optical components are disposed on common platform, the components may be otherwise connected together so that, by altering a length of test arm 130, a length between the ophthalmic apparatus and the eye is also altered. For example, they may be disposed in, and directly or indirectly mechanically connected to an instrument housing using any suitable technique. With an instrument configured in such a manner, the housing may be moved to achieve a change in test arm length and alignment of apparatus 175. It will be appreciated that, in the illustrated embodiment, it is assumed that the subject's eye will remain stationary during an alignment procedure (e.g., by placing the patient's head on a chin rest 125 and/or forehead rest) and instrument 100 is moved to achieve alignment between the instrument and the eye. However, in other embodiments, a patient's head (including their eye) may be moved to achieve alignment. In such embodiments, it is not necessary that any particular connection between the interferometer 105 and ophthalmic apparatus 175 exist. For example, processor 145 may be programmed to control movement of the subject's eye by moving the head and/or chin rest until alignment is achieved (i.e., by varying a length of a test arm).

Figure 2B:
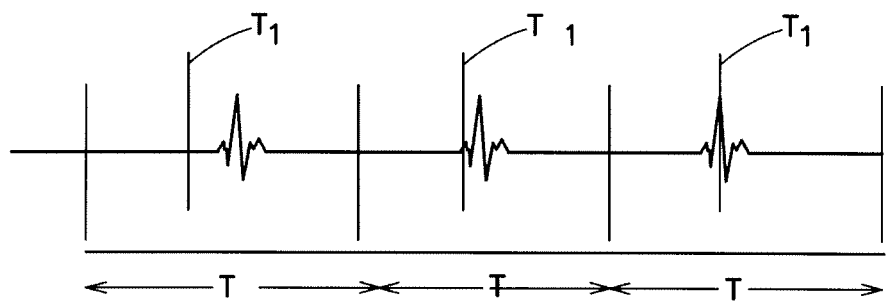
FIG. 2B is a graphical illustration of an example output from the display of the instrument in FIG. 2A.

As is conventionally known, in some embodiments, mirror 140 is moved back and forth in an oscillatory manner (i.e., scanned as shown by arrow A) such that the components of the output signal of detector 160 that are attributed to interference (i.e., interference spikes) form a relatively high-frequency component of the signal. In some embodiments, a controller is adapted to control the oscillatory movement. An output of the detector can be presented on a display 185. An example of such an output is shown in FIG. 2B. In the illustrated output, time period T corresponds to a period of one oscillation of the mirror.

It will be appreciated that, in embodiments in which mirror 140 is so oscillated, the predetermined length is achieved at a particular time $T_1$ in period T. In such embodiments, the mirror may be manually positioned prior to oscillation to achieve the predetermined length at the particular time. As shown in FIG. 2B, the output of the detector can be observed and the test arm length adjusted until interference occurs at time $T_1$ corresponding to the predetermined length in period T. Typically, an interference pattern for a given source corresponds to an envelope of spikes in the detector output, and the test arm length is adjusted such that a peak in the envelope occurs at the appropriate time $T_1$.

Although, in the above embodiment, a relatively high-frequency component was achieved by oscillatory movement of mirror 140, in other embodiments, such a component is achieved by altering the optical path length for example by rotating a cube 142 about an axis D in the path of the reference beam.

Figure 3:
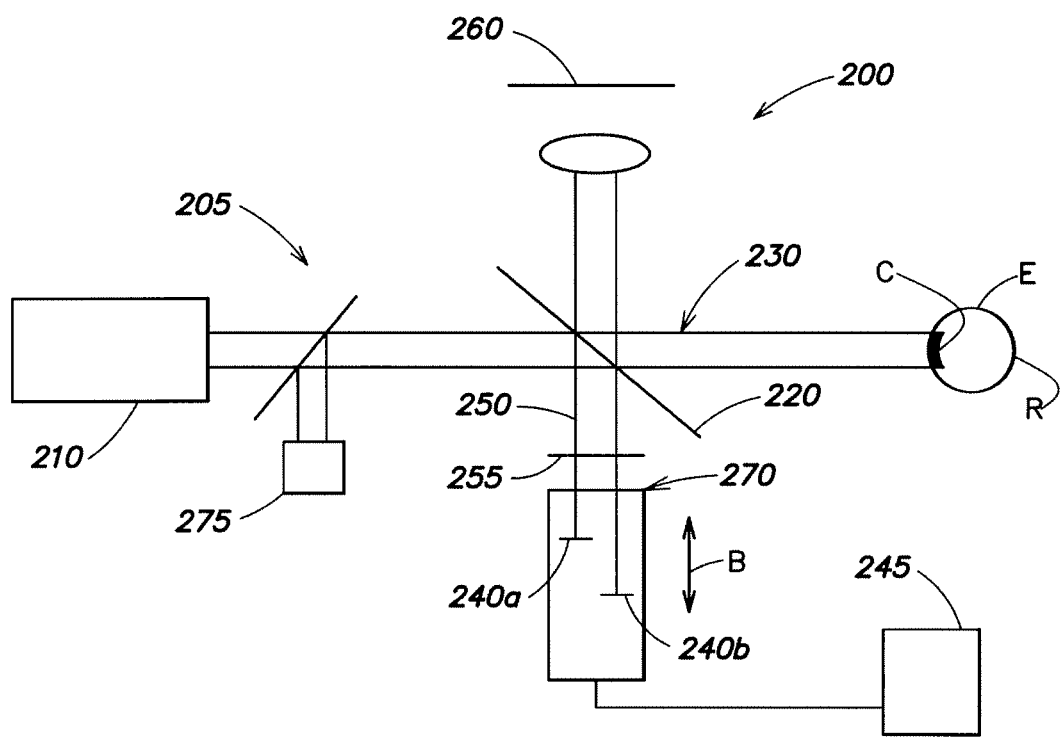
FIG. 3 is a schematic illustration of another example of an ophthalmic instrument according to aspects of the present invention.

FIG. 3 is a schematic illustration of another example of an ophthalmic instrument 200 according to aspects of the present invention for use with a subject's eye E. The instrument comprises an interferometer 205 and an ophthalmic apparatus 275. Similar to the embodiment discussed above, the interferometer and the apparatus are configured and arranged such that an adjustment of a test arm of the interferometer relative to an eye results in a corresponding adjustment of a distance from ophthalmic apparatus 275 to the eye.

In interferometer 205, light from a source 210 is projected onto a beam splitter 220 which projects light onto an eye E in a test arm 230 and into a reference arm 250. However, in contrast to the apparatus of FIG. 2A, the reference arm includes two mirrors 240a and 240b and a portion of the light is projected onto both mirrors. An output signal from a detector 260 is generated by combining a reflection by the eye with reflections from mirrors 240a and 240b. The amplitude of the signal will increase due to interference when the length of either or both portions of the reference arm is equal to a length in the test arm that corresponds to a reflective surface of the eye.

In some embodiments, the interferometer constitutes a portion of an apparatus used to measure eye dimensions. Further details of such axial length measurement device are given in U.S. Patent Applic. No. 2005/0140981 to Waelti (hereinafter referred to as Waelti) and U.S. patent application Ser. No. 11/954,146, by Lai, filed Dec. 11, 2007 (hereinafter referred to as Lai). The substance of both of said applications is hereby incorporated by reference.

In instrument 200, one of said mirror 240a and 240b (assumed to be mirror 240a in the discussion below) is positioned to produce a reference beam to interfere with light reflected from a surface of eye (e.g., the anterior surface of cornea C). According to aspects of the present invention, mirror 240a is positioned such that the reference arm has a predetermined length. In some embodiments, the positioning mirror 240a and/or mirror 240b may be achieved using a suitably programmed processor 245. In other embodiments, mirror 240a and/or mirror 240b may be moved using a manually operated stage (not shown).

For example, in some embodiments, mirror 240a may be precisely positioned using techniques described above for mirror 140. In yet other embodiments, mirror 240a may be fixed in a single location relative to the beam splitter such that the portion of the reference beam corresponding to mirror 240a has a fixed length. In embodiments where the interferometer constitutes a portion of a device to measure eye dimension, it will be appreciated that mirror 240a may be fixed. In such embodiments, mirror 240b is adjustable to achieve interference with another surface of the eye (i.e., a surface other than the front surface of the cornea, such as a retinal surface), so that an eye length can be measured.

Once mirror 240a is appropriately positioned such that the predetermined reference arm length is achieved, the test arm 230 is adjusted relative to eye E, which results in a corresponding adjustment of a distance from the ophthalmic apparatus 275 to eye E. The adjustment of the test arm is made to achieve interference between the light reflected from a surface of the eye and the light reflected from the mirror. In the illustrated embodiment, the positioning is achieved using techniques described above for adjusting the test arm (e.g., by moving eye E and/or instrument 200).

As stated above, according to aspects of the present invention, ophthalmic apparatus 275 is connected to interferometer 205 such that, by altering a length of test arm, an optical length between the ophthalmic apparatus and the eye is also altered. It will be appreciated that by so altering a test arm length the ophthalmic apparatus can be accurately, axially aligned with the eye. It will also be appreciated that the instrument is configured such that, when the test arm is made to achieve interference between the light reflected from a surface of the eye and the light reflected from the mirror, the ophthalmic apparatus is operatively positioned relative to the eye.

As described above, optical components of the interferometer are connected to optical components of the interferometer such that by altering a length of test arm, a length between the ophthalmic apparatus and the eye is also altered.

As discussed above, with reference to FIG. 2, in some embodiments, a relatively high-frequency signal component can be generated in the detector output. In the illustrated embodiment, a mirror in the reference arm may be moved back and forth such that the components of the output for the detector that are attributed to interference form a relatively high-frequency component of the signal. In the embodiment of FIG. 3, both mirrors 240a and 240b may be so moved as described in Waelti. For example, in some embodiments, the mirrors are provided on a platform 270 that is oscillated back and forth (as indicated by an arrow B) toward and away from beam splitter 220. As discussed above, in such embodiments, the predetermined length is achieved at regular intervals (i.e., a time $T_1$ with a period T) and the length of the test arm may be adjusted such that interference occurs at the particular time $T_1$.

In some embodiments, an interferometer is implemented using fiber optics. Example of such an apparatus is given in Waelti and Lai, both of which were incorporated by reference above.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An ophthalmic instrument for use with a subject's eye, comprising:
   an interferometer having a test arm in which the subject's eye is to be positioned and a reference arm, the reference arm including a mirror, the instrument adapted to position the mirror such that the reference arm has a predetermined length;
   an ophthalmic apparatus mechanically coupled to the interferometer such that, by altering a test arm length, a length between the ophthalmic apparatus and the eye is also altered; and
   a detector positioned to receive a combination of light reflected from the eye and light reflected from the mirror, whereby, when the mirror is positioned to achieve the predetermined length and a length of the test arm is adjusted such that interference between the light reflected from the eye and the light reflected from the mirror is achieved, the ophthalmic apparatus is optically aligned with the eye.

2. The instrument of claim 1, wherein the apparatus comprises at least one of:
   a portion of an ablation laser apparatus, a portion of an aberrometer, a portion of a topographer, and a portion of a pachymeter.

3. The instrument of claim 1, wherein the interferometer constitutes a portion of a device used to measure an axial eye length.

4. The instrument of claim 1, further comprising a processor coupled to the mirror and configured to position the mirror.

5. The instrument of claim 1, wherein the mirror is adapted to be manually positioned.

6. The instrument of claim 1, wherein optical components of the interferometer and optical components of the apparatus are connected to a common platform.

7. The instrument of claim 1, wherein the optical components of the interferometer and optical components of the apparatus are disposed in and connected to a housing.

8. The instrument of claim 1, wherein a portion of the instrument is adapted to be moved to achieve alignment with the eye.

9. The instrument of claim 1, wherein the instrument is adapted to move the eye to achieve alignment with the eye.

10. The instrument of claim 1, wherein the instrument is adapted to move the mirror in an oscillatory manner, such that the predetermined length is achieved at a particular time, and optical alignment of the ophthalmic apparatus with the eye is achieved when the test arm length is adjusted such that the interference occurs at the particular time.

11. The instrument of claim 1, wherein the reference arm includes a second mirror.

12. A method of alignment, comprising:
   providing an ophthalmic instrument comprising an ophthalmic apparatus and an interferometer having a test arm and a reference arm, the reference arm including a mirror, the ophthalmic apparatus mechanically coupled to the interferometer such that, when a test arm length is altered, a length between the ophthalmic apparatus and an eye is also altered;
   positioning the mirror such that the reference arm has a predetermined length;
   projecting partially coherent light, a first portion of the light directed onto the eye in the test arm, and a second portion of the light directed onto the mirror in the reference arm;
   combining a portion of the light reflected from the eye and a portion of the light reflected from the mirror;
   adjusting a length of the test arm such that interference between the light reflected from the eye and the light reflected from the mirror is achieved and optical alignment of the ophthalmic apparatus with the eye is achieved.

13. The method of claim 12 wherein, in the step of providing, the ophthalmic apparatus comprises at least one of: a portion of an ablation laser apparatus, a portion of an aberrometer, a portion of a topographer, and a portion of a pachymeter.

14. The method of claim 12 wherein, in the step of providing, the interferometer constitutes a portion of a device used to measure an axial eye length.

15. The method of claim 12, further comprising a step of using a processor to position the mirror to achieve the predetermined length.

16. The method of claim 12, further comprising a step of manually positioning the mirror to achieve the predetermined length.

17. The method of claim 12, wherein the step of adjusting comprises moving the optical components of the interferometer and the optical components of the apparatus on a common platform.

18. The method of claim 12, wherein the step of adjusting comprises moving the optical components of the interferometer and the optical components of the apparatus in a housing.

19. The method of claim 12, wherein the step of adjusting comprises moving a portion of the instrument to achieve alignment with the eye.

20. The method of claim 12, wherein the step of adjusting comprises moving the eye to achieve alignment with the eye.

21. The method of claim 12, further comprising moving the mirror in an oscillatory manner, such that the predetermined length is achieved at a particular time, and wherein the step of adjusting comprises adjusting the test arm length until the interference occurs at the particular time.

\* \* \* \* \*